United States Patent [19]

Binder

[11] Patent Number: 5,766,244
[45] Date of Patent: Jun. 16, 1998

[54] INTRAOCULAR ARTIFICIAL LENS AND METHOD FOR FABRICATING SAME

[76] Inventor: Helmut Binder, Stösselstr. 6, Schweinfurt, D-8720, Germany

[21] Appl. No.: 725,338

[22] Filed: Oct. 1, 1996

Related U.S. Application Data

[63] Continuation of Ser. No. 150,078, filed as PCT/DE92/00418 May 22, 1992, abandoned.

[30] Foreign Application Priority Data

May 23, 1994 [DE] Germany .......................... 41 16 869.0

[51] Int. Cl.⁶ .......................................... A61F 2/16
[52] U.S. Cl. .......................................... 623/6
[58] Field of Search .......................................... 623/6

[56] References Cited

U.S. PATENT DOCUMENTS

| | | | |
|---|---|---|---|
| 3,925,825 | 12/1975 | Richards et al. | 623/6 |
| 4,014,049 | 3/1977 | Richards et al. | 623/6 |
| 4,085,467 | 4/1978 | Rainin et al. | 623/6 |
| 4,242,760 | 1/1981 | Rainin | 623/6 |
| 4,262,370 | 4/1981 | Hartstein | 623/6 |
| 4,316,291 | 2/1982 | Severin | 623/6 |
| 4,403,354 | 9/1983 | Rainin | 623/6 |
| 4,404,694 | 9/1983 | Kelman | 623/6 |
| 4,504,981 | 3/1985 | Walman | 623/6 |
| 4,629,462 | 12/1986 | Feaster | 623/6 |

FOREIGN PATENT DOCUMENTS

| | | | |
|---|---|---|---|
| 0053384 | 6/1982 | European Pat. Off. | 623/6 |
| 90/11061 | 10/1990 | WIPO | 623/6 |

*Primary Examiner*—Mary Beth Jones
*Attorney, Agent, or Firm*—Cohen, Pontani, Lieberman, Pavane

[57] ABSTRACT

An intraocular artificial lens for placement in an eye having an interior chamber and a posterior chamber, the intraocular artificial lens having a planar lens body configured to be arrangeable in the posterior chamber of the eye and at least one spirally shaped haptic fastener fixed to the lens body. The haptic fastener includes a posterior chamber portion with a first end connected to the lens body and being configured to extend spirally from a peripheral edge of the lens body so that the posterior chamber portion forms a support segment that is elastically supportable in a posterior chamber angle of the eye, a penetration portion arranged at a second end of the posterior chamber portion so as to curve out of the plane of the lens body so as to be passable through an iridectomy, and an anterior chamber portion connected to the penetration portion so as to be parallel to the plane of the lens body.

31 Claims, 6 Drawing Sheets

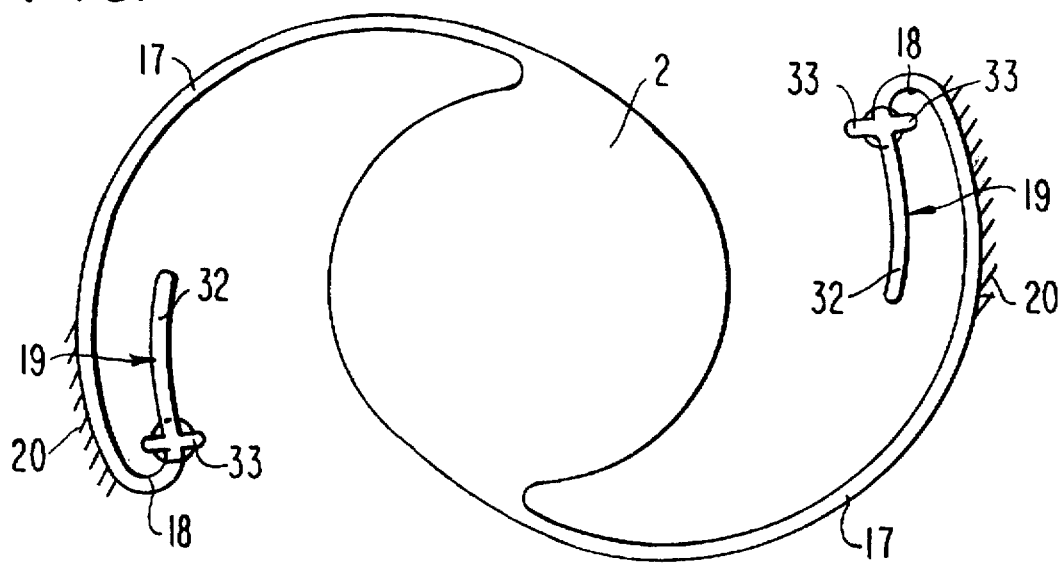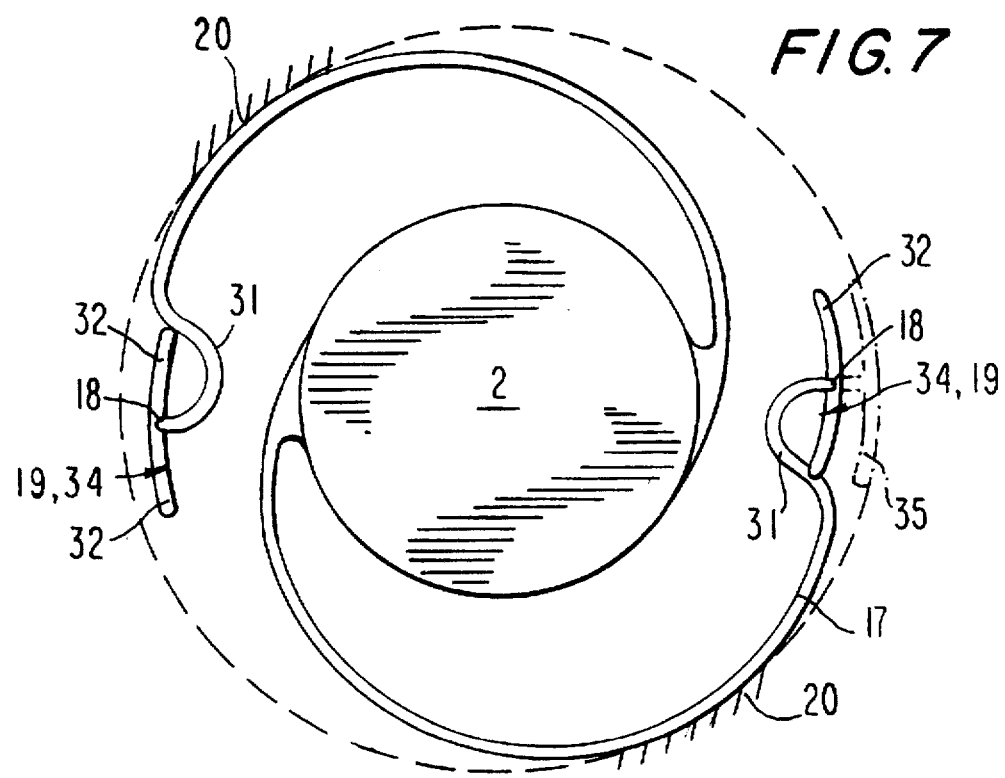

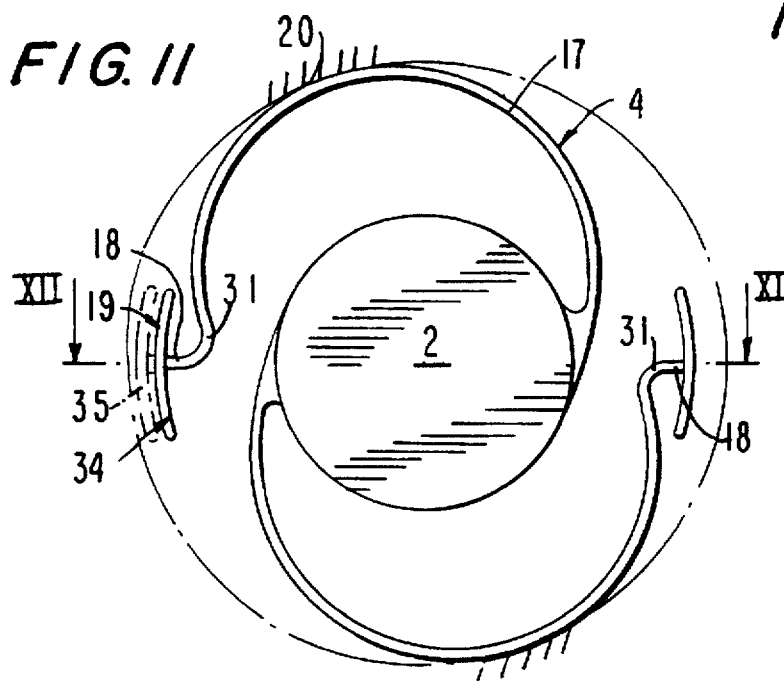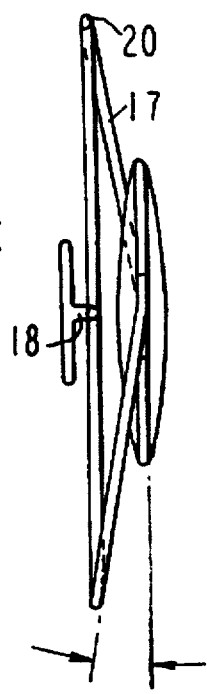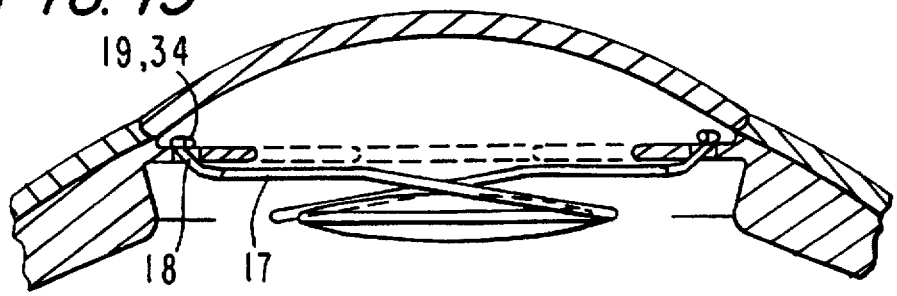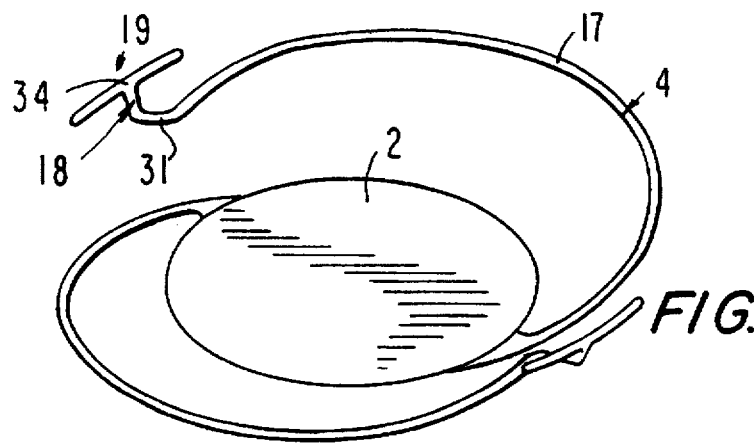

INTRAOCULAR ARTIFICIAL LENS AND METHOD FOR FABRICATING SAME

This is a continuation application under 37 C.F.R. §1.53 of U.S. Pat. application Ser. No. 08/150,078, filed as PCT/DE92/00418 May 22, 1992 now abandoned.

BACKGROUND OF THE INVENTION

1. Field of the Invention

The inventions relates to an intraocular artificial lens for replacement of the lens of the eye (posterior chamber lens), as used for example in cataract operations.

2. Description of the Prior Art

The hitherto customary methods of implanting an artificial lens precisely in the location of the natural lens of the eye, i.e. in the so-called posterior chamber, are all extremely difficult to perform. This is so because it is important to fix the artificial lens securely in this location without damaging structures of the eye, and at the same time to minimize both the time and the surgical work required for the operation.

Various methods of implantation are known using various types of artificial lens, such as described for example in Fechner "Intraokularlinsen, Grundlagen und Operationslehre", second edition, Ferd. Enke Verlag, Stuttgart 1984, in particular page 128 ff.

Thus, for example for so-called "extracapsular cataract extraction", i.e. when the posterior lens capsule is preserved, an artificial lens is implanted whose haptic fasteners lie either in the capsule sac or in the posterior chamber angle (sulcus ciliaris).

When the lens capsule is not preserved (frequently it tears when the damaged lens is removed), an additional means of support must be used. For example, the artificial lens can be fixed by sewing the haptic fasteners to structures of the eye, e.g. the ciliary body. However, this damages the structures of the eye and bleeding can occur inside the eye. In addition, the sewing is difficult and complicated and takes a lot of time.

It is also possible to effect the fixture by creating an artificial membrane (drawing in threads) which prevents the lens from slipping rearwards in the direction of the vitreous humor. This method has essentially the same disadvantages as described previously.

Therefore, it was proposed as an alternative for every operation that an artificial lens be implanted as far as possible in the original location of the natural lens lying either on the iris, in the form of a so-called iris clip, or even in front of it, in the form of a so-called anterior chamber lens (EP-A1-03 46 245). These anterior chamber lenses present a continual hazard for structures of the anterior portion of the eye such as the cornea, chamber angle and iris. In addition, the function of the iris, in particular the pupil, is considerably impaired by the iris clip. Serious irritating conditions are often caused by permanent rubbing between the surface of the lens and the surface of the iris.

It is also known for the artificial lens to be supported by haptic fasteners both in the anterior chamber and in the posterior chamber. Thus, U.S. Pat. No. 4,366,582 and U.S. Pat. No. 4,316,291 each show a lens supported by means of two haptic fasteners in the anterior chamber (passed through the pupil and resting on the outer periphery of the iris) and by means of two further haptic fasteners in the posterior chamber. In addition, U.S. Pat. No. 4,316,291 proposes a spine penetrating through the iris from the front to the rear.

A lens is known from German reference 31 40 465 with a supporting element for the posterior chamber of the eye and a fastener which is passed through an incision in the iris into the anterior chamber and there surrounds the iris concentrically in a ring and presses against the supporting element in the posterior chamber resiliently in the manner of a clip.

U.S. Pat. No. 4,242,760 describes a lens which is also supported in the posterior chamber. One of the haptic fasteners extends through the iris aperture/pupil, runs a short distance radially in front of the same and then passes through a peripheral incision back into the posterior chamber again where the curved end piece then rests on the sulcus.

Moreover, U.S. Pat. No. 4,504,981, in particular FIGS. 9 and 12, discloses an artificial lens which exhibits two mirror-symmetrical haptic fasteners running in opposite directions with two recognizably different portions, namely a posterior chamber portion curved in a slightly concave manner from the edge of the lens body, and an anterior chamber portion running in the opposite direction parallel with the anterior chamber angle. Through an end area of the posterior chamber portion these haptic fasteners pass through a relatively peripheral iridectomy out of the posterior chamber into the anterior chamber where the anterior chamber portion is supported lying on the iris. Thus, this known lens is attached by means of the anterior chamber portions of the haptic fasteners in the iris and at the same time supported on the iris. Displacement or unscrewing from this suspension of the lens or its haptic fasteners is prevented in that the fasteners are embodied so that they run in opposite directions. These haptic fasteners need not have a special elasticity since they are not supported in any of the eye chamber angles but are only attached in the iris and secured by their running in opposite directions through the passages through the iris. However, the fact that these haptic fasteners are embodied so that they run in opposite directions makes their introduction and fixture very complex and the clamping effect in the iris can also prevent their movement or lead to irritation. The lenses are only fixed in position radially through the arrangement of the iridectomies and attachment of the haptic fasteners by means of these. Elastic radial support, e.g. in the sulcus ciliaris, ensuring precisely central arrangement of the lens regardless of the production of the iridectomies during the operation, is not guaranteed.

Lastly, U.S. Pat. No. 4,404,694 discloses a lens which has a first haptic fastening element mounted in the lens capsule and a second haptic fastening element mounted by its end portion in the anterior chamber angle and passing through the iris in the peripheral area.

SUMMARY OF THE INVENTION

The object of the present invention is to provide an intraocular artificial lens which allows easy relatively rapid implantation with the lens body (optic) disposed in the posterior chamber in the location of the natural lens, universal application, secure fixture and the minimum possible danger to structures of the eye. In addition, another object of the invention is to provide an economical method for manufacturing the inventive artificial lens.

According to the invention, this object is achieved through an intraocular artificial lens having at least one haptic fastener that is fixed to the lens body disposed in the posterior chamber of the eye so that the lens body is supported both in the posterior chamber angle (sulcus ciliaris) and in the anterior chamber. Starting from the lens body, in succession, the haptic fastener includes a posterior chamber portion with a posterior chamber supporting segment, a penetration portion curved out of the plane of the lens body and running through a relatively peripheral iridectomy, and an anterior chamber portion running parallel with the plane of the lens body. The advantage of this is that firstly the optic (lens body) lies in the posterior chamber in the position of the removed natural lens, and secondly the lens is fixed by means of the at least one haptic fastener in the anterior chamber so that it is visible from the front and at the same time cannot slip towards the rear, i.e. is securely positioned. Here, the support can be provided by the haptic fastener on the peripheral rim of the iris or further outwards radially in the anterior chamber angle.

In a further embodiment of the invention, the penetration portion runs through the iridectomy essentially perpendicular or at an angle to the iris. Here the penetration portion which is inclined obliquely or disposed at an angle, can essentially run in a diametral plane perpendicular to the lens body or to the iris. Here, the course of the penetration portion from the posterior chamber portion to the anterior chamber or to the anterior chamber portion is obviously radially upwards at an oblique angle in the direction of the anterior chamber. It is advantageous if the essentially arc-shaped posterior chamber portion is connected with the penetration portion by means of an inward arc. This produces the great advantage that when the artificial lens according to the invention is produced, the haptic fasteners can be fabricated completely from solid material in the plane of the lens, after which only the penetration portion has to be raised to the desired inclination. Then, the penetration portion can be formed or bent into an angled or a perpendicular position.

The penetration portion passing through the iridectomy obliquely or at an angle can also be disposed in a plane running essentially tangentially to the iris. Then, the penetration portion can be formed from the normal arc of the posterior chamber portion into the desired angular position.

It is particularly advantageous if two or more haptic fasteners are disposed on a lens body and if these are essentially identical to one another. This ensures very secure positioning. It is extremely advantageous if the support by the haptic fasteners is provided simultaneously both in the anterior chamber and in the posterior chamber. This gives an optimum guarantee of secure fixture perpendicular to the plane of the lens. This is achieved if in addition to the supporting segment in the anterior chamber, the haptic fasteners also have a supporting segment in the posterior chamber by means of which support is provided in the posterior chamber angle (sulcus ciliaris).

The dual-chamber support of the haptic fasteners according to the invention even makes it possible to provide just a single haptic fastener on a lens body (optic) if the iris is also clamped securely between the supporting segments by the support. As a result, the clamping haptic fastener according to the invention performs the role of a clip, with the exception that the lens lies in the natural lens plane and not in the same plane as the iris as in the case of a conventional iris clip. In addition, the iris is not clamped securely in its central area which is of greatest importance for its function, but on the periphery which is not so functionally important (no obstruction to contraction of the pupil).

However, optimum positioning/fixture is obtained if at least two haptic fasteners are used. Particularly gentle fixture is achieved if the haptic fasteners emerge from the lens body in the form of an archimedean spiral for example and the support is provided by means of segments of this spiral. Here it is important that the respective ends of the supporting segments are set back at least slightly towards the inside, allowing gentle support even when relatively short.

According to another embodiment of the invention, the support of the haptic fastener can be provided through the anterior chamber portions in different zones of the iris.

Thus, for example, the support can be provided by means of the anterior chamber portions on the peripheral rim of the iris, and this can essentially be effected level with the iridectomy or a portion of the iris lying further out or in the anterior chamber angle. This depends on the form and the course of the anterior chamber portion. Particularly gentle, practically punctiform support in the anterior chamber can be achieved if the anterior chamber portion is bent back in the form of a loop relatively far past the penetration portion, and the portion adjoining the penetration portion can either follow a spiral course or run in the opposite direction to this. It is advantageous if the supporting arm running back is also swept back so that the bent off arc/arc portion and the supporting end are in each case bent or guided in the direction of the supporting surfaces, allowing only very short, practically punctiform support. According to the invention, the loops are guided such that the return portion runs either peripherally (outside) or centrally (inside) in relation to the penetration portion. When the loop arm return portion runs on the inside, two-point support is guaranteed with maximum safety, even if the penetration segment runs very close to the periphery. A planar, correspondingly rounded widening of the supporting end, preferably with a manipulating opening provided in it, is extremely advantageous. However, the ends can also be bent back to form an essentially closed ring or an eye.

A great variety of embodiments of the anterior chamber portion are possible within the scope of the invention. For example, only a single relatively short supporting arm can be provided with a shorter hook arm cantilevered in the opposite direction. Another possible embodiment has two arms which are essentially symmetrical in relation to the penetration portion and are embodied so that they can be made to collapse or fold together for passage through the iridectomy. The anterior chamber portion can also be embodied in the form of an arm running in the opposite direction to the posterior chamber portion, and after emerging from the iridectomy, this arm can follow an essentially parallel course of the posterior chamber portion or a tangential course. To guarantee reliable attachment, at least one transverse arm running essentially perpendicular to the attaching arm and thus essentially radially in relation to the lens body or the iris can be provided at the start of the attaching arm. The provision of two identical transverse arms running in opposite directions radially guarantees particularly reliable fixture and attachment of the anterior chamber portion. Naturally, the attaching arm can also be aligned or guided essentially following the further spiral course of the posterior chamber portion, i.e. running in the same direction as the posterior chamber portion, and the anterior chamber portion is reliably prevented from slipping out through the iridectomy into the posterior chamber by the transverse arms. This embodiment can also be produced relatively inexpensively since in each case a haptic fastener must be made with a suitable length and with two small transverse arms. Then only the penetration portion is formed so that the parallel alignment of the attaching arm is retained. In this way, the anterior chamber portion is raised or disposed on a higher plane, i.e. the plane of the surface of the iris.

However, the posterior chamber portion can also consist solely of two attaching arms which run in opposite directions and are symmetrical in relation to the iridectomy and to the penetration portion, producing an anterior chamber suspension. Here, this anterior suspension consisting of two attaching arms can be disposed on any embodiment of the penetration portion. Thus, in one embodiment the posterior chamber portion can be guided essentially in the form of a spiral or arc to essentially below the iridectomy, after which the penetration portion is aligned for example perpendicular to the iris. However, this can also be aligned obliquely in relation to the iris from the course of the posterior chamber portion.

In a further embodiment the anterior chamber suspension can be attached to an oblique radial penetration portion which is connected by means of an inward arc to the posterior chamber portion. This embodiment is also a favorable variant from the production standpoint since here it is possible to fabricate the haptic fasteners in the plane of the lens conventionally by turning and milling from a single piece of material. After this, the penetration portion is bent out of the plane of the lens obliquely in a radial plane so that the double-armed suspension is swivelled parallel to the original position. This embodiment can also be produced optimally in a conventional manner only entailing removal of material if the oblique angle of the penetration portion is so great that the suspension and the penetration portion do not lie in the same tangential vertical plane and thus practically no burrs under the suspension arms have to be removed later in a separate production step.

The anterior chamber suspension can also be embodied so that the two attaching arms are essentially aligned radially to the iris and to the lens body. However, here it is expedient to keep these arms relatively short, i.e. the outer peripheral arm must be shorter than the distance of the iridectomy to the anterior chamber angle. In order to obtain reliable suspension and at the same time avoid irritating contact at the anterior chamber angle, at least the outwardly directed attaching arm must be bent backward or forward in an arc in comparison with the course of the posterior chamber portion. From a production standpoint, this is also an advantageous embodiment (for production by removal of material and subsequent thermal forming) since the penetration portion can be bent out of the posterior chamber portion at an appropriate angle. When the attaching arms are embodied with curved ends, it is expedient to guide these back into a plane essentially parallel with the plane of the lens or iris by appropriate counter bending.

According to the invention, the anterior chamber portion preferably begins with a radial part which essentially runs radially and at the same time parallel with the iris. This means that the haptic fastener runs with its penetration portion perpendicular or at a slightly oblique angle to the iris through the iridectomy and beyond this only over a relatively short distance and, at the same time, essentially parallel to the iris and essentially radially outwards or radially inwards (radial part) so as to subsequently pass into the respective supporting, attaching and suspension arms and parts of the anterior chamber portion, described previously.

Here, the radial part can have an only relatively small longitudinal or radial extension. It is sufficient if through the radial part the following portion begins so that it does not lie in the same tangential plane with the penetration portion. It is thus sufficient if the radial part exhibits a length which is at least equal to the diameter of the penetration portion. This is the case for example if the next part of the anterior chamber portion, e.g. the two-armed suspension, is not seated on the penetration portion in the form of a T, but runs essentially tangentially on the external periphery/surface of its outer end. This embodiment of the haptic fastener, in particular its anterior chamber portion, means that when the artificial lens is produced in a conventional manner solely by turning and then milling, there is/are no material/burrs to be removed later between the penetration portion and the anterior chamber portion. Because of the very tiny dimensions of the artificial lens, subsequent removal of burrs is very time consuming and expensive and entails a significant risk of breakage.

As already mentioned previously, the radial part can run inwards or outwards, depending on the form of the other parts of the anterior chamber portion and/or depending on the intended radial distance of the iridectomy from the rim of the iris. It can be seen that from a production viewpoint, the radially outward course of the radial part is more advantageous, in particular if the posterior chamber portion ends in an inward arc. However, an inwardly guided radial part can be advantageous if no externally open inward arc is present, but the posterior chamber portion for example only exhibits its slight spiral inward curvature or this curvature is slightly increased inwards at the end of the portion.

Consequently, according to the invention the form of the haptic fasteners is such that they support the lens body located in the posterior chamber both in the sulcus ciliaris and also at the same time in the anterior chamber. Here, the elongation of the arm lying in the sulcus runs through peripheral openings in the iris (iridectomies) into the anterior chamber so that the specially shaped ends of the haptic fasteners come to lie in the anterior chamber angle, for example, or lie above the iris. The advantages of this design include:

1. the lens body lies precisely in the location of the natural lens;
2. very gentle support in the sulcus and possibly with punctiform support in the anterior chamber angle, or attachment over very short portions of the iris;
3. there is practically no adverse effect on the function of the iris since the contacts between the haptic fasteners and the iris are punctiform or over very tiny portions and the iris function (dilation, contraction of the pupil) is fully assured;
4. the lens can be used in all cases which necessitate implantation of an artificial lens since it is in no way dependent on the presence or absence of a supporting membrane (rear part of the lens capsule);
5. the lens is easy to implant:
    no ancillary operation is necessary,
    the procedure for introduction into the posterior chamber is similar to that with conventional posterior chamber lenses,
    the creation of iridectomies is standard in almost all lens implantation procedures,
    one highly unsatisfactory point with conventional posterior chamber lenses is the uncertainty about the position of the fasteners since these are no longer visible after implantation; poorly seated fasteners can lead to major problems (e.g. so-called "trapped iris"); with the lens according to the invention the fasteners are clearly visible and their position is easy to adjust intraoperatively;
6. the lens is usable universally in all cases:
    as a so-called "stand-by lens" for "extracapsular cataract extraction" (ECCE),
    for all "intracapsular cataract extractions" (ICCE) (complete removal of the capsule sac),
    for all secondary operations, for protection of the iris for operations on the posterior portions of the eye entailing silicone replacement of the vitreous humor, as a substitute for anterior chamber lenses and the so-called iris clip lenses;

7. minimum possible threat to structures of the eye, e.g. through rubbing on sensitive surfaces, through diversion of the flow of aqueous humor, among other things;

8. the lens is secured extremely well:

the part of the haptic fasteners lying in the anterior chamber prevents rearward movement in the direction of the vitreous humor and also provides circumferential/rotational stability; consequently it is impossible for the lens to be "lost" in the vitreous humor;

in addition, the special loop, hook or curved form of the part of the haptic fasteners lying in the anterior chamber prevents the lens from sliding away through the iridectomies.

According to the invention, in one preferred embodiment the artificial lens with the at least one haptic fastener is formed in one piece, i.e. the intraocular artificial lens is fabricated from one piece of material.

In a further embodiment the lens body with the at least one haptic fastener is formed in more than one piece, and the at least one haptic fastener is secured to the lens body in a manner known per se, for example by direct bonding or introduction of the end of the haptic fastener in a corresponding peripheral hole and subsequent bonding.

Overall, it can be said that with the artificial lens according to the invention the operation on the eye becomes much simpler and shorter. In addition, a better result is obtained and above all the long-term prognosis is significantly improved. It is even conceivable that the method currently found to be best (ECCE) can be dropped since the preservation of the rear part of the capsule is no longer necessary (the remaining part of the capsule can develop fibrosis and necessitate a subsequent second intervention— capsulatomy). This operation frequently fails since the capsule tears. In addition, lens residues often remain which can cause problems later. None of this applies with the lens according to the invention since the natural lens can simply be removed complete with the capsule. Thus, the artificial lens according to the invention can be used for practically all lens replacement operations without restrictions.

The present invention further provides a method for producing the inventive lens. In the method the lens body together with the haptic fasteners is produced by turning and subsequent milling in initial steps so that the haptic fasteners and all their portions (posterior chamber, penetration and anterior chamber portion) essentially lie in the plane of the lens body. Then, in at least one subsequent step, at least the penetration portion is progressively formed or swivelled out of the plane of the lens into a perpendicular or angled position. This can be carried out thermally for example depending on the material used. Then, depending on the form of the anterior chamber portion, this can also be formed or guided back into an alignment parallel with the plane of the lens.

Here, it is pointed out again that by disposing a radial part at the start of the anterior chamber portion, it is possible to produce the artificial lens in a very advantageous conventional manner, namely solely by turning and milling, without subsequent removal of burrs.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

FIG. 6 shows a plan view of an artificial lens in a further embodiment, with a tangential anterior chamber attaching arm and two transverse arms;

FIG. 7 shows a plan view of a further embodiment of the artificial lens, with two tangential anterior chamber attaching arms and an oblique penetration portion;

FIG. 11 shows a plan view of a further embodiment of the artificial lens, with an anterior chamber suspension, a radial oblique penetration portion and an inwardly directed arc;

FIG. 12 shows a side view of the artificial lens in FIG. 11;

FIG. 13 shows a section along the line XII—XII in FIG. 11;

FIG. 14 shows a perspective view of the artificial lens as in FIG. 11, illustrating the course of the haptic fastener portions;

DETAILED DESCRIPTION OF THE PREFERRED EMBODIMENTS

Figure 1:
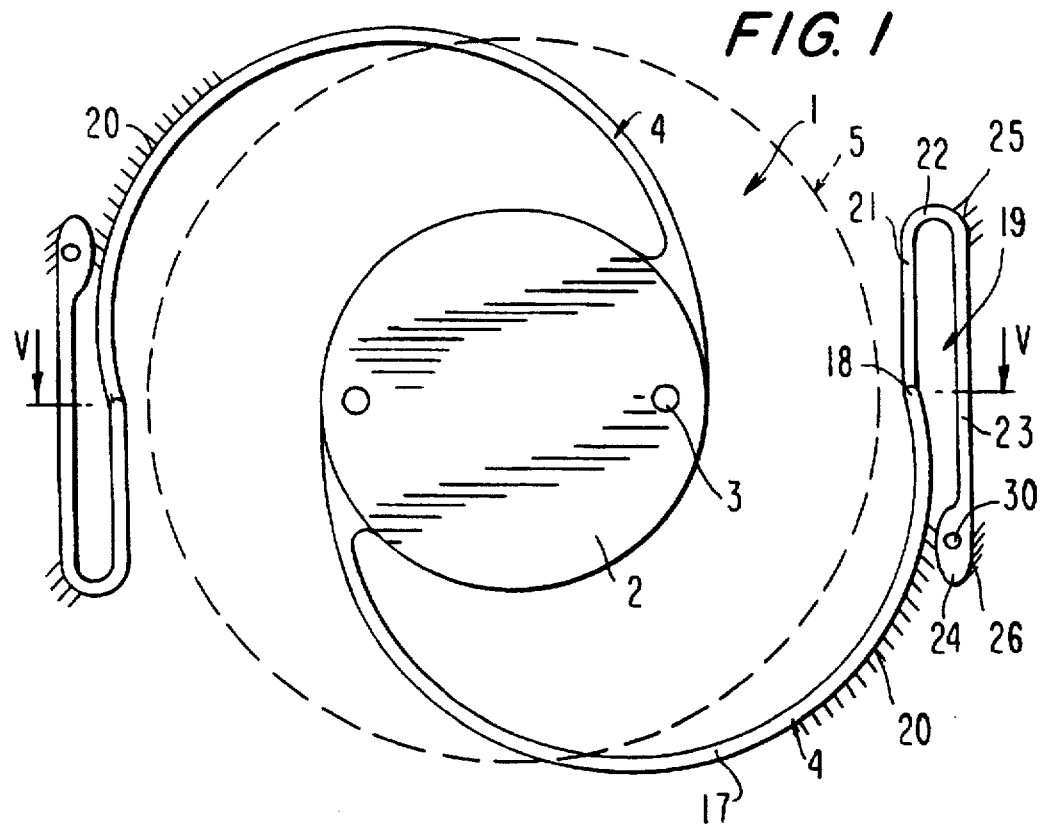
FIG. 1 shows a plan view of an artificial lens with two haptic fasteners with an arm of the anterior chamber portion running back peripherally.
Figure 3:
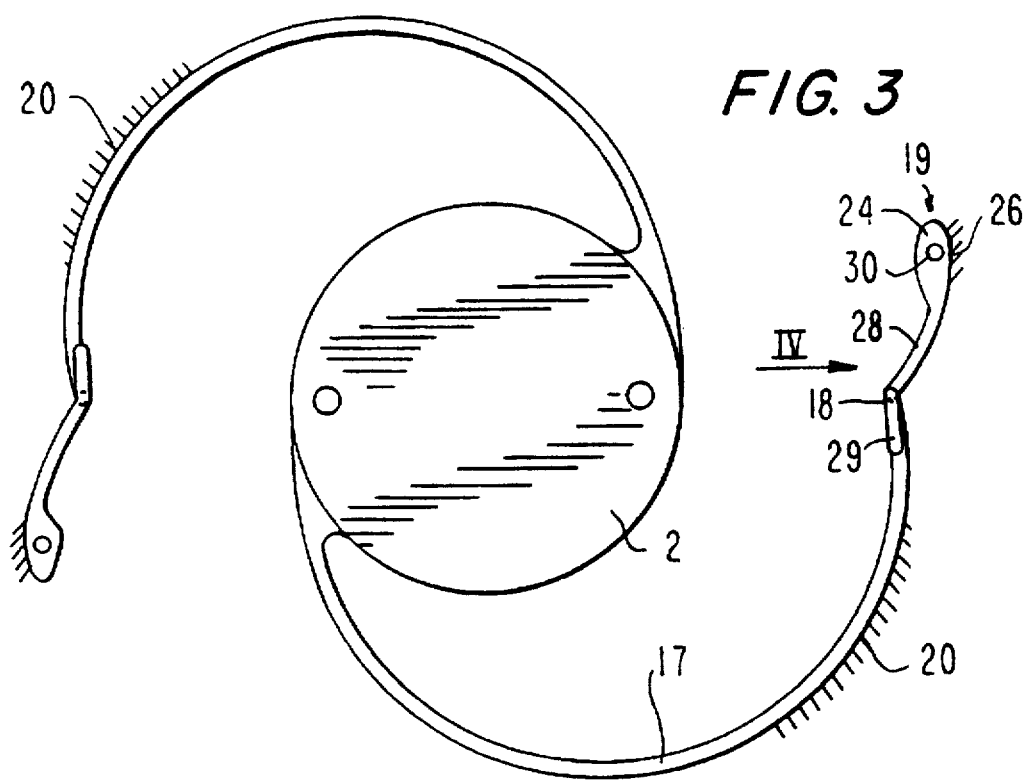
FIG. 3 shows a plan view as in FIG. 1, with the anterior chamber portion in a further embodiment (with a supporting arm and counter hook)

It can be seen rom FIG. 1 in conjunction with FIG. 3 that the intraocular artificial lens 1 according to the invention is composed of a disc-shaped lens body 2 in which at least two manipulating openings 3 are provided. The drawing does not show the optic of the lens which is incorporated in the lens body 2 in a manner known per se.

Two spirally shaped haptic fasteners 4 are formed, in each case rotationally symmetrically, on the outer circumference of the lens body 2. The haptic fasteners 4 are relatively thin and elastic. They can easily be compressed in the direction of the lens body 2 and laid for example in the sulcus ciliaris (posterior chamber angle) 5 shown with broken lines.

Figure 5:
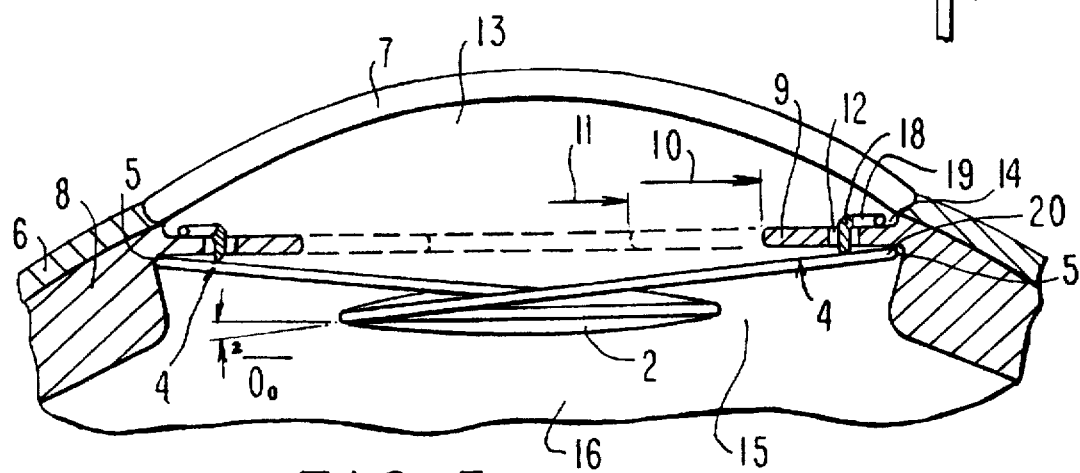
FIG. 5 shows a section along the line V—V in FIG. 1, at the same time showing a partial section through an eyeball with an implanted artificial lens pursuant to the present invention.

In order to be able to provide a more precise description of the construction of the artificial lens according to the invention and in particular its specific manner of fixture in the eye, first a brief description should be given of the construction of the front part of the eyeball, as shown in section in FIG. 5.

The eyeball is surrounded by the sclera 6 which in its front part runs into the transparent cornea 7. On the inside of the sclera 6 adjoining the cornea 7 there is the essentially annular ciliary body 8 which runs into the iris 9. The ciliary body 8 has an annular recess, the sulcus ciliaris or posterior chamber angle 5 towards the iris. The iris 9 can open and close annularly as is known and in the process adopt the "dilated pupil" position 10 or "contracted pupil" position 11 (shown by the broken line). Iridectomies or penetration openings 12 for passage of fluid are almost always made for eye operations, preferably at the peripheral rim of the iris 9.

The iris 9 divides the front portion of the eyeball into an anterior chamber 13 and a posterior chamber 15. The anterior chamber 13 is visible from the front and forms an annular anterior chamber angle 14 between the iris 9 and the cornea 7. The posterior chamber 15, which, as already mentioned previously, exhibits the sulcus ciliaris or posterior chamber angle 5 between the ciliary body 8 and the iris 9, is located behind the iris 9 in the direction of the vitreous humor 16.

It can be seen from FIG. 1 in conjunction with FIG. 5 that from the standpoint of their course in the two chambers of the eye the haptic fasteners 4 can be divided into different portions. Thus, it is possible to speak of a posterior chamber portion 17 which is inclined at an angle of approximately 10° to the plane of the lens, of a penetration portion 18 which essentially runs perpendicular to the plane of the lens, and lastly of an anterior chamber portion 19 which essentially runs parallel with the lens body 2.

At its end lying next to the penetration portion 18, the posterior chamber portion 17 is forced radially inwards somewhat, departing from the normal spiral course, so that when lying in the posterior chamber angle/sulcus cilaris 5, the posterior chamber portion 17 is only supported over a part of its periphery, the posterior chamber supporting segment 20, as indicated in the drawing by the shading.

According to the invention the anterior chamber portion 19 can be embodied in various ways, as shown in FIGS. 1 to 4.

Figure 2:
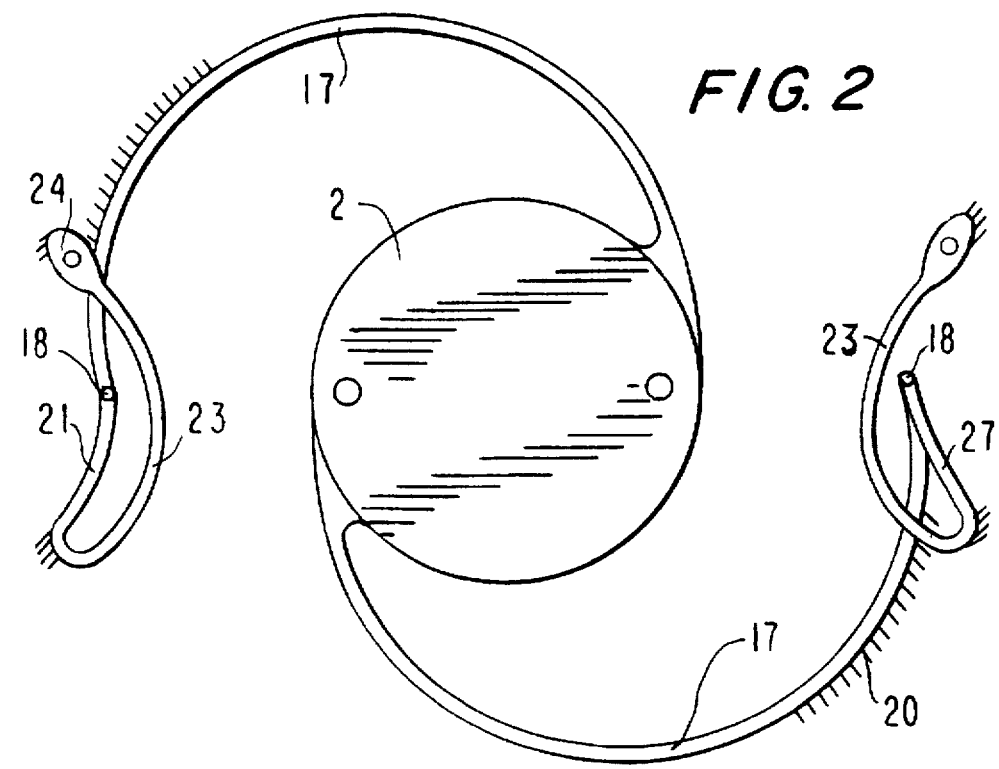
FIG. 2 shows a plan view as in FIG. 1, with a portion running centrally, each of the two haptic fasteners exhibiting a different form.

Thus, FIG. 1 shows one embodiment and FIG. 2 two different embodiments of anterior chamber portions 19 in which in each case the portion 19 follows an essentially loop-shaped course. In each case the essential point is that in the first part of its course, extending from the penetration portion 18, the anterior chamber portion 19 exhibits a starting arm 21 which runs via a supporting arc 22 into a supporting arm 23 running in an opposite direction to the arm 21. The supporting arm 21 has a supporting end 24. The supporting arm 23 receives practically punctiform support in the anterior chamber angle 14 by means of very short segments, i.e. the supporting arc segment 25 and the supporting end segment 26, indicated by the shading lines.

In the embodiment of the anterior chamber portions 19 of the haptic fasteners 4 shown in FIG. 1, the supporting arm 23 is disposed peripherally in relation to the penetration portion 18, while in the embodiments shown in FIG. 2 the supporting arms 23 are in each case guided centrally, i.e. so they run inwards relative to the lens 2. Here, the starting arm 21 of the left-hand anterior chamber portion in FIG. 2 is essentially formed in the spiral course of the haptic fastener, as in the embodiment in FIG. 1, while the embodiment shown on the right in FIG. 2 exhibits a starting arm 27 which is formed in the opposite spiral direction.

Figure 4:
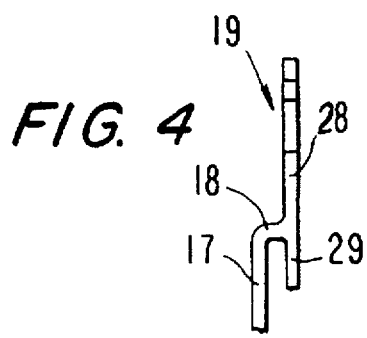
FIG. 4 shows a view in the direction of arrow IV in FIG. 3.

FIGS. 3 and 4 show a further variant of the anterior chamber portion 19. This fourth embodiment does not have a loop-shaped design but only a supporting arm 28 which essentially corresponds to the end half of the supporting arm 23 shown in FIG. 1, and terminates in a widened supporting end with a supporting segment 26. In essentially the opposite direction to the supporting arm 28 there is a short hook arm 29 which prevents the supporting arm 28 from slipping out through the iridectomy 12. The respective supporting ends 24 of the supporting arms 23, 28 can also be provided with manipulating openings 30 which make it easier to bring the anterior chamber portion into the supporting position.

The supporting end 24 can be embodied as an eye or take the form of an annular essentially closed arc, instead of a widening with a manipulating opening 30.

The introduction/fixture of the intraocular artificial lens according to the invention in the eye is very simple. Depending on the number of haptic fasteners 4, first two or more iridectomies 12 are created evenly distributed on the periphery of the iris 9. This is standard and is performed for almost any eye operation. After introducing the artificial lens 1 into the posterior chamber 15, with the haptic fasteners 4 slightly compressed, the supporting ends 24 are in each case passed through the iridectomies 12 and, for example in the embodiment shown in FIG. 1, first turned clockwise until the supporting arms 23 protrude as far as the arc position 22. Then, the assembly is turned counter-clockwise until the starting arms 21 appear in their entirety in the anterior chamber 14 and the penetration portions 18 are drawn into the iridectomies 12. These are quiet simple turning and displacing movements which are facilitated in particular by the manipulating openings 3, 30.

In the embodiment shown in FIG. 3, after introduction of the supporting ends 24 through the iridectomy 12, it is only necessary to move the assembly counter-clockwise until the iridectomy comes up against the penetration portion 18, after which the iridectomy of the very elastic iris 9 is widened and drawn over the hook arm 29 releasing the latter, after which the iridectomy or the iris lies elastically around the penetration portion 18.

In the further embodiment shown in FIG. 6 the anterior chamber portion 19 consists of an attaching arm 32 which is essentially aligned so that it runs in the opposite direction to the posterior chamber portion 17. Obviously, this can also be aligned so that it runs in the same direction. At the end next to the penetration portion 18 the attaching arm 32 exhibits two essentially radially aligned transverse arms 33 which prevent the attaching arm 32 from slipping out through the iridectomy 12.

In the embodiment of the artificial lens shown in FIG. 7, the anterior chamber portion 19 has two attaching arms 32 running in opposite directions and symmetrical with the penetration portion 18. The arms 32 are disposed essentially parallel to and at a distance from the anterior chamber angle and form an anterior chamber suspension 34. In this embodiment the penetration portion 18 is formed perpendicular to the iris. Here, the end of the posterior chamber portion 17 next to the penetration portion 18 takes the form of an inward arc 31, relative to the lens body 2, the arc end of which essentially points radially outwards, relative to the lens body 2.

In the case of the end of the haptic fastener shown on the right in FIG. 7, the anterior chamber suspension 34, 35 is additionally drawn in with the dash-dotted line. The illustration shows the anterior chamber portion 19 and the suspension 24, 35 in a phase of production in which these portions together with the penetration portion 18 still have not been formed from the first plane of machining (e.g. material-removing machining) into the plane parallel offset function plane of the anterior chamber portion with the perpendicular or angled position of the penetration portion.

Figure 8:
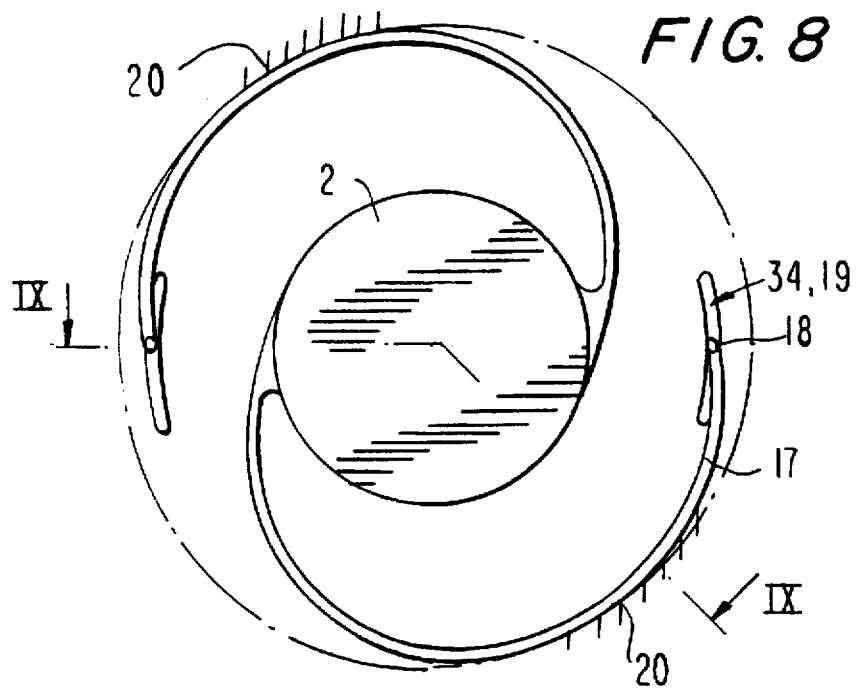
FIG. 8 shows a further embodiment of the artificial lens with anterior chamber attaching arms as in FIG. 7, with a perpendicular penetration portion.
Figure 9:
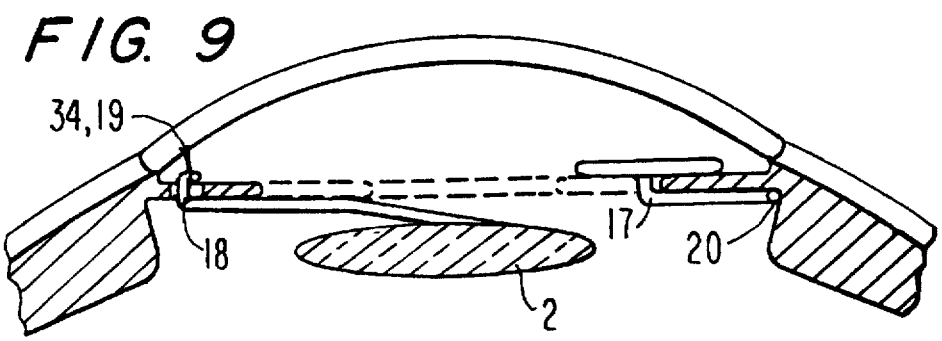
FIG. 9 shows a section through the artificial lens in FIG. 8 along the line IX—IX.
Figure 10:
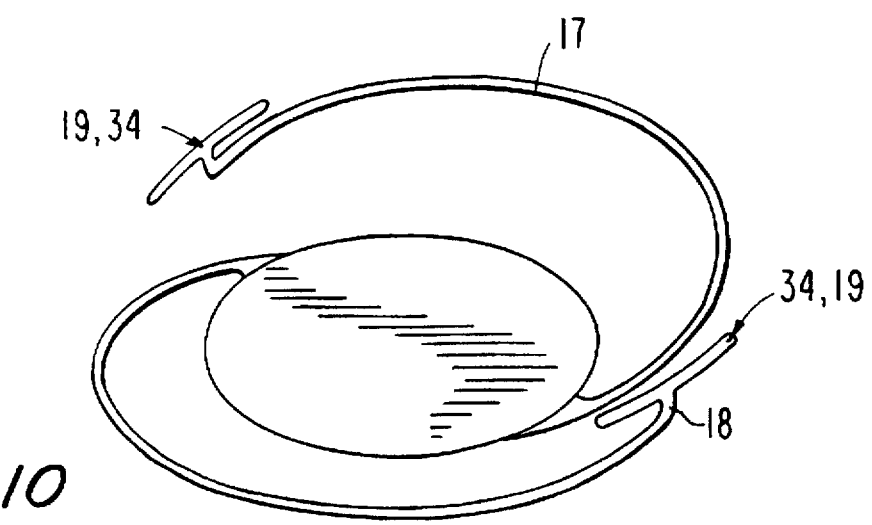
FIG. 10 shows a perspective view of the artificial lens in FIG. 8, illustrating the alignment of the haptic portions.

In the embodiment shown in FIGS. 8 to 10 the anterior chamber portion 19 is essentially identical to that in FIG. 7. However, here the penetration portion 18 is bent directly from the course of the posterior chamber portion (essentially swivelled tangentially) and essentially runs perpendicular to the iris. Here, the arrangement and design of the portions of the haptic fasteners are clearly visible, in particular in the perspective view in FIG. 10.

The embodiment shown in FIGS. 11 to 14 is a further variant of the embodiment in FIG. 7. Whereas in the embodiment in FIG. 7 the penetration portion 18 runs essentially perpendicular to the iris, in the embodiment shown in FIGS. 11 to 14 the penetration portion 18 runs essentially at an oblique angle or radially at an angle to the iris. There the penetration portion 18 is practically bent directly from the inwards arc 31 (swivelled radially), as is clearly visible in particular in FIGS. 11, 13 and 14. In FIG. 11 the broken line shows the position of the anterior chamber suspension 34 on the left-hand haptic fastener prior to being bent out of the plane of the lens. It will be apparent that relatively advantageous production is possible in the plane of the lens, after which the penetration portion 18 is bent out of the plane.

It can be seen from FIGS. 12 and 13 in comparison with in particular FIGS. 5 and 9 that the shaping of the posterior chamber portion can also vary, in particular as regards its angular alignment to the iris. Thus, for example, a posterior chamber portion can be inclined at a constant angle, as shown in FIG. 5. However, in its first part the posterior chamber portion can also be inclined at a steeper angle essentially as far as the supporting segment 20, whereas the further part leading to the penetration portion runs essentially parallel with the iris.

Figure 15:
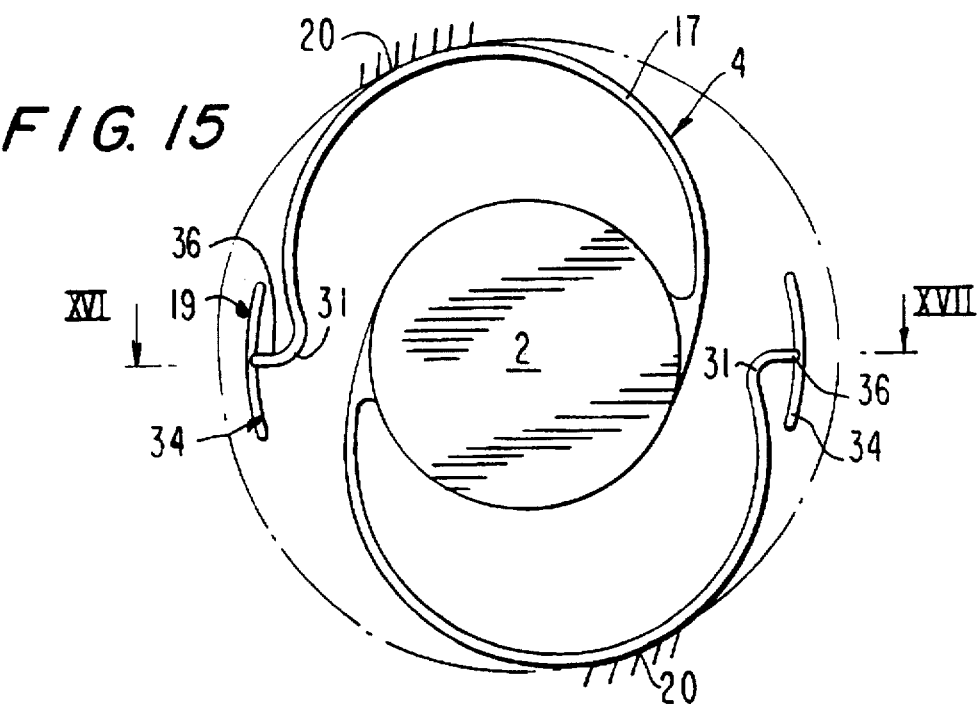
FIG. 15 shows a plan view of an artificial lens in another embodiment, with a radial part on the anterior chamber portion.
Figure 16:
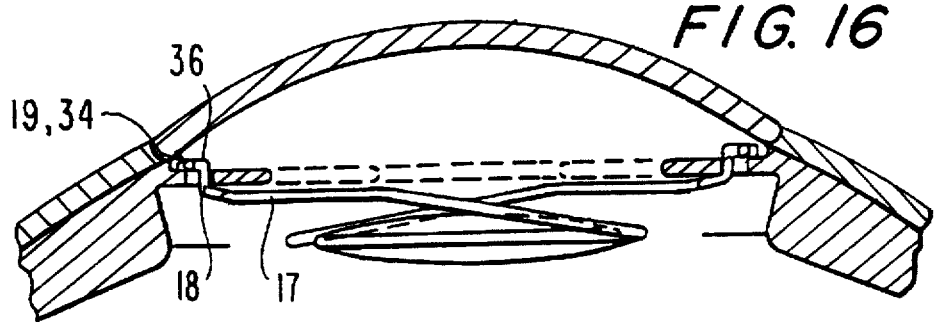
FIG. 16 shows a section along the line XVI—XVI in FIG. 15.
Figure 17:
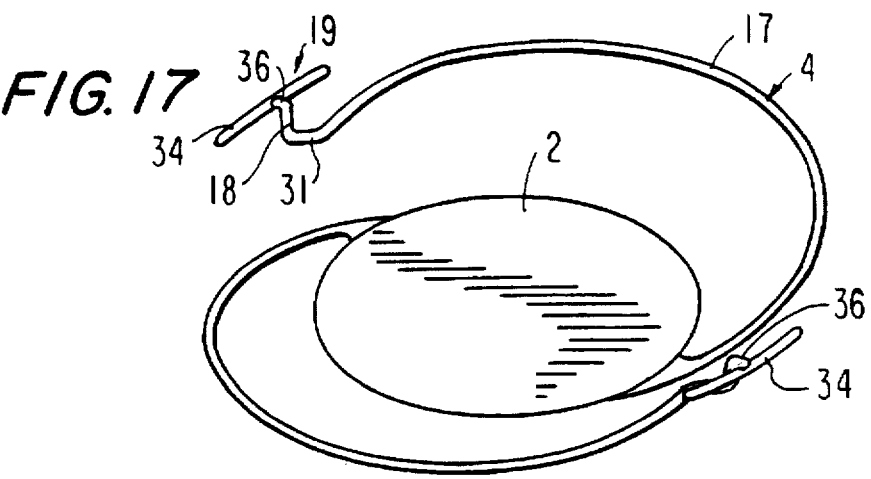
FIG. 17 shows a perspective view of the artificial lens as in FIG. 15, illustrating the design of the haptic fasteners.

The embodiment shown in FIGS. 15 to 17 is a further variant of the embodiments shown in FIG. 7 and FIGS. 11 to 14. It can be seen that the interior chamber portion 19, which here exhibits a double-armed suspension 34, additionally has a radial part 36 between the suspension 34 and the penetration portion 18. The suspension 34 is moved radially outwards by the radial part 36 which lies in the same horizontal plane with the suspension 34 and in essentially the same radial vertical plane with the penetration portion 18. It can be seen that the radial part 36 can also be disposed so that it runs inwards, with the result that the suspension is located on the inside in relation to the iridectomy 12 and the penetration portion.

The radial part 36 can be provided per se in any of the artificial lenses shown in the figures described previously. The posterior chamber portion end, penetration portion and anterior chamber portion (with the radial part) must each be embodied or disposed in relation to one another so that none of the portion parts comes to lie in the same tangential vertical plane.

The invention is not limited by the embodiments described above which are presented as examples only but can be modified in various ways within the scope of protection defined by the appended patent claims.

I claim:
1. An intraocular artificial lens for placement in an eye having an iris, an anterior chamber and a posterior chamber, the intraocular artificial lens comprising:
 a lens body configured to be arrangeable in the posterior chamber of the eye and defining a plane; and
 at least one curved haptic fastener fixed to the lens body, the haptic fastener being formed of a plurality of portions, including:
  a first, posterior chamber portion with a first end connected to the lens body and being configured to extend tangentially from a peripheral edge of the lens body and curved so that the posterior chamber portion forms a support segment that is elastically supportable in a posterior chamber angle of the eye;
  a second, penetration portion arranged at a second end of the posterior chamber portion so as to curve out of the plane of the lens body so as to be passable through an iridectomy; and
  a third, anterior chamber portion connected to the penetration portion so as to be substantially parallel to the plane of the lens body.
2. An intraocular artificial lens according to claim 1, wherein the penetration portion is configured to extend substantially perpendicular to the plane of the lens body.
3. An intraocular artificial lens according to claim 1, wherein the penetration portion is configured to extend at an angle to the plane of the lens body.
4. An intraocular artificial lens according to claim 3, wherein the penetration portion is configured to extend in a substantially perpendicular diameter plane relative to the lens body.
5. An intraocular artificial lens according to claim 4, wherein the haptic fastener further includes a radial transition portion between the penetration portion and the support segment of the posterior chamber portion, the transition portion being configured as an arc that curves inwardly from the support segment of the posterior chamber portion toward the lens body.
6. An intraocular artificial lens according to claim 3, wherein the penetration portion is configured to extend in a plane substantially tangential to the lens body.
7. An intraocular artificial lens according to claim 1, wherein at least two haptic fasteners are mounted on the lens body.
8. An intraocular artificial lens according to claim 1, wherein the anterior chamber portion is configured to be engagable at a radially outermost peripheral rim of the iris.
9. An intraocular artificial lens according to claim 1, wherein the anterior chamber portion is configured so as to be engagable with an anterior chamber angle of the anterior chamber of the eye.
10. An intraocular artificial lens according to claim 1, wherein the haptic fastener is configured so as to have segments that are relatively short and are engagable with portions of the eye so as to support the lens.
11. An intraocular artificial lens according to claim 1, wherein the anterior chamber portion of the haptic fastener is configured to have a starting arm that extends from the penetration portion, and a supporting arm that extends from the starting arm in an opposite direction.
12. An intraocular artificial lens according to claim 11, wherein the supporting arm has a first portion extending from the starting arm, and a second end portion, the first and second portions being configured and arranged so as to provide a two-point contact with the iris.
13. An intraocular artificial lens according to claim 11, wherein the supporting arm is configured so as to extend radially outside the penetration portion, relative to the lens body.

14. An intraocular artificial lens according to claim 11, wherein the supporting arm is configured so as to run radially inside the penetration portion, relative to the lens body.

15. An intraocular artificial lens according to claim 11, wherein the starting arm of the anterior chamber portion is configured to have a curved shape and the supporting arm is configured to have a curved shape.

16. An intraocular artificial lens according to claim 12, wherein the second end portion of the supporting arm is configured to extend inwardly and is wider than a remainder of the supporting arm, an aperture being arranged in the second end portion.

17. An intraocular artificial lens according to claim 12, wherein the second end portion of the supporting arm has a circular arc configuration.

18. An intraocular artificial lens according to claim 1, wherein the anterior chamber portion has a support arm that extends from the penetration portion substantially in the direction of the posterior chamber portion, the anterior chamber portion further having a hook arm that extends from the penetration portion in a direction opposite the support arm, the support arm and the hook arm being arranged to lie in a common plane.

19. An intraocular artificial lens according to claim 1, wherein the anterior chamber portion includes a first support arm arranged to extend from the penetration portion and a second support arm arranged to extend from the penetration portion as a mirror image of the first support arm, the first and second support arms being configured to be displaceable in a single plane with the penetration portion so as to be passable through an iridectomy.

20. An intraocular artificial lens according to claim 1, wherein the anterior chamber portion includes at least one attachment arm arranged to extend above the penetration portion.

21. An intraocular artificial lens according to claim 20, wherein the at least one attachment arm is configured to run in a direction opposite to the posterior chamber portion.

22. An intraocular artificial lens according to claim 20, wherein the attachment arm is configured to run in a common direction with the posterior chamber portion.

23. An intraocular artificial lens according to claim 20, wherein at least one transverse arm is provided on the attachment arm above the penetration portion, the at least one transverse arm being configured so as to be essentially radially directed relative to the lens body.

24. An intraocular artificial lens according to claim 23, wherein two essentially identical transverse arms are provided on the attachment arm so as to run radially in opposite directions.

25. An intraocular artificial lens according to claim 20, wherein two attachment arms are provided so as to extend from the penetration portion in opposite directions so as to form a suspension that is substantially symmetrical to the penetration portion.

26. An intraocular artificial lens according to claim 1, wherein the anterior chamber portion is connected to the penetration portion by a radial part which extends substantially radially and parallel to the lens body.

27. An intraocular artificial lens according to claim 26, wherein the radial part extends radially outwardly relative to the lens body.

28. An intraocular artificial lens according to claim 1, wherein the posterior chamber portion is configured so that the support segment lies essentially in a plane parallel to the lens body, the second end of the posterior chamber portion being curved inwardly toward the lens body, the penetration portion extending substantially perpendicularly from the second end of the posterior portion.

29. An intraocular artificial lens according to claim 1, wherein the posterior chamber portion of the haptic fastener is connected to the lens body so as to be inclined at an angle of approximately 10° to the lens body plane.

30. An intraocular artificial lens according to claim 1, wherein the lens body and the at least one haptic fastener are formed as a single piece.

31. An intraocular artificial lens according to claim 1, wherein the at least one haptic fastener and the lens body are separate parts, the at least one haptic fastener and the lens body being bonded together.

* * * * *